US00PP35867P2

(12) United States Plant Patent
Hansen

(10) Patent No.: US PP35,867 P2
(45) Date of Patent: Jun. 11, 2024

(54) ***NEPETA* PLANT NAMED 'CHARTREUSE ON THE LOOSE'**

(50) Latin Name: ***Nepeta* hybrid**
Varietal Denomination: Chartreuse on the Loose

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,589

(22) Filed: Nov. 7, 2023

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

The new and distinct hardy perennial *Nepeta* plant named 'Chartreuse on the Loose' has a broad, low-spreading mound, with compact habit and arching to horizontal stems. The new plant begins flowers in late spring and, continues until fall frost without deadheading. The flowers are lavender-blue with persistent rosy-purple calyces just above the complementing bright chartreuse-yellow, cordate, fragrant foliage. The new plant is useful in the landscape en masse, as an accent, or in containers to bring color and fragrance to a garden and attract butterflies and hummingbirds.

1 Drawing Sheet

Botanical denomination: *Nepeta* hybrid.
Variety designation: 'Chartreuse on the Loose'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2023, followed by the "Walters Gardens 2023-2024 Catalog" initially released on May 19, 2023. The claimed plant was first sold on Apr. 24, 2023, to Centerton Nursery by Walters Gardens, Inc., who obtained the plant and all information relating from the inventor. No plants of *Nepeta* 'Chartreuse on the Loose' have been sold or offered for sale in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to a new and distinct cultivar of *Nepeta* named 'Chartreuse on the Loose'. The new plant was selected as a single seedling selected from the progeny of a cross between the proprietary unreleased hybrid known only as 15-11-2 (not patented) as the female or seed parent and the proprietary unreleased hybrid known only as 15-22-1 (not patented) as the male or pollen parent. The pollination was directed by the inventor in the summer of 2016. The seed was harvested later in the summer of 2016, grown out, evaluated in subsequent years, and a single seedling was selected and assigned the breeder code 16-6-1 for the trial period prior to naming. 'Chartreuse on the Loose' was approved in a final evaluation in the summer of 2020 and slated for later introduction. The new plant was selected based on compact habit, flower cover, foliage color, and a long blooming season. The new plant has been asexually propagated first by division in the late summer of 2018 followed by tip cuttings with the resultant plants remaining identical to the original plant, stable and true to type in successive generations.

SUMMARY OF THE INVENTION

*Nepeta* 'Chartreuse on the Loose' is different from its parents and all other Catmint cultivars known to the inventor. The nearest comparison plants known to the inventor include: 'Limelight' (not patented), 'Citriodora' (not patented), 'Cat's Pajamas' U.S. Plant Pat. No. 31,127, 'Kitten Around' U.S. Plant Pat. No. 30,940, and 'Purrsian Blue' U.S. Plant Pat. No. 24,788.

'Limelight' has a smaller habit, the foliage is smaller and less yellowish, and flowers for a shorter period. 'Citriodora' has a larger habit, green to grey-green foliage and shorter flower spikes of light lavender flowers. 'Cat's Pajamas' is a more rounded habit and has foliage that is a deeper green. 'Puritan Blue' has a larger habit, smaller more purplish-blue flowers, and the foliage is deeper green. 'Kitten Around' has a smaller rounded habit and the foliage is deeper green.

The female parent has smaller and less yellowish foliage, the flowering was over a shorter period, and the habit is more rounded and opened up in the middle at flowering. The male parent has a flatter and more spreading habit, with larger foliage that was less yellowish and deeper chartreuse.

The present invention has not been evaluated under all possible environmental conditions. The phenotype may vary with changes in the environment such as light, temperature, water, nutrient availability, etc. without a change in the genotype of the plant. *Nepeta* 'Chartreuse on the Loose' is unique from all other Catmint known to the inventor in the following combined traits:

1. The habit is rounded, short, and compact with arching to horizontal stems;
2. Foliage is cordate, small with crenate teeth, and has an herbal fragrance;
3. Leaf color is bright chartreuse-yellow;
4. Flowers are large, lavender-blue with persistent rosy-purple calyces just above the foliage;
5. Plant flowering starts in late spring and continues without deadheading until frost.

BRIEF DESCRIPTION OF THE DRAWINGS

The photographs of the new plant *Nepeta* 'Chartreuse on the Loose' are of a two-year old plant in a full-sun, trial garden in Zeeland, Michigan and demonstrate the unique aspects of the new plant. The colors are as accurate as reasonably possible with color reproductions. Ambient light spectrum, temperature, source, and direction may cause the appearance of minor variations in color.

DETAILED PLANT DESCRIPTION

Figure 1:
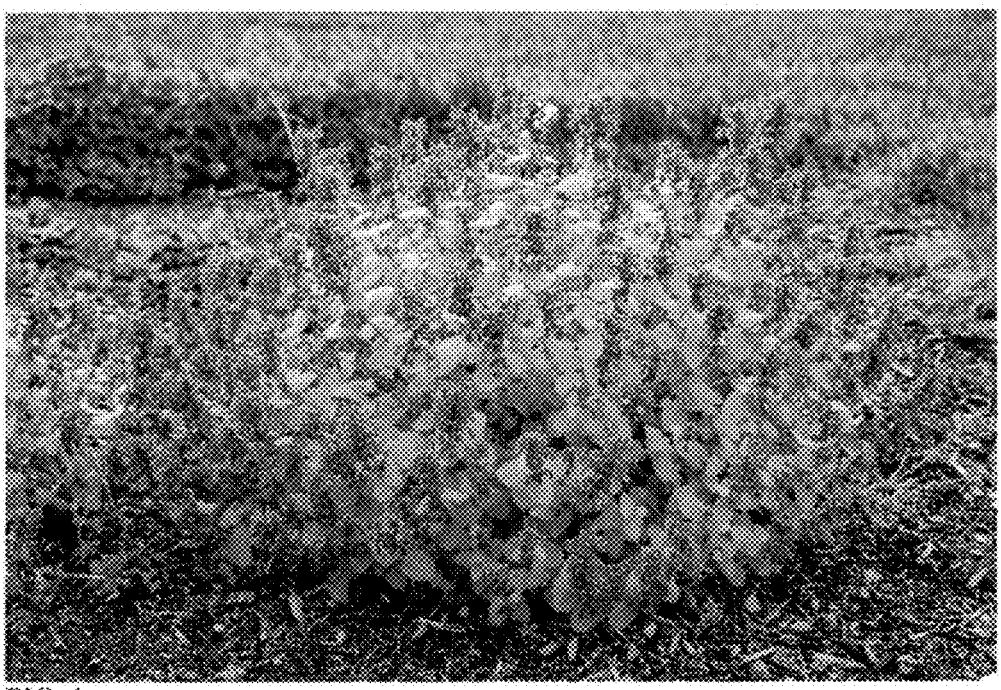
FIG. 1 shows the overall habit of the new plant.
Figure 2:
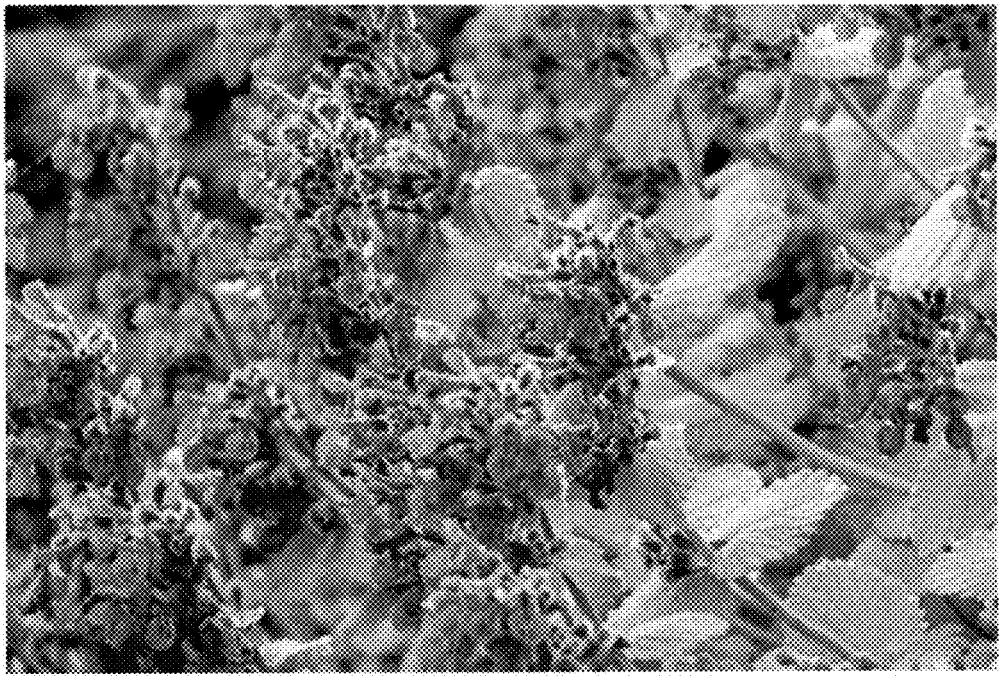
FIG. 2 shows a close-up of the flowers, buds, and stems.

The following descriptions are based on a two-year-old plant of *Nepeta* 'Chartreuse on the Loose' grown in a full-sun trial garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture, and maturity levels, but without any change in the genotype.

Parentage: Female parent is the proprietary hybrid 15-11-2; male parent is the proprietary hybrid 15-22-1;

Plant habit: Herbaceous perennial; multi-stemmed, foliage mounding to about 42 cm tall and 90 cm wide at the base and 49 cm tall in flower;

Growth: Rapid; time to initiate roots at 23° C. about one week; finishing in a standard #1-15 cm container in about 8 to 10 weeks from rooted 25 mm plug;

Root: Fine, freely branching; color between RHS NN155C and RHS 158D depending on soil type and nutrient content;

Foliage: Opposite; simple; cordate; rugose on both abaxial and adaxial surfaces; margins crenate with 12 to 19 teeth per side; micro-puberulent on adaxial and abaxial surfaces; apex acute; base cordate; blade size to about 47 mm long and 39 mm wide near base, average about 32 mm long and 20 mm across;

Foliage fragrance: Foliage and stem with herbal fragrance;

Leaf color: Variable; young expanding adaxial between RHS 144A and RHS 145A and nearest RHS 145A, young expanding abaxial between RHS 146D and RHS 145A and nearest RHS 145A; mature adaxial between RHS N144A and RHS 146D and nearest RHS N144D, mature abaxial between RHS 145B and RHS 145C;

Venation: Longitudinal; impressed on adaxial surface and costate on abaxial surface;

Vein color: Adaxial between RHS 144A and RHS N144D, abaxial nearest RHS 145C;

Petiole: Micro-puberulent adaxial and abaxial; slightly concavo-convex; to about 16 mm long and 2 mm across at base; average about 7 mm long and about 1.5 mm across;

Petiole color: Adaxial between RHS 146D and RHS 145A, abaxial between RHS 146D and RHS 145C;

Stem: Puberulent; quadrangular; arching to horizontal; heavily branched; about 58 cm long and 3 mm across at base; about 40 stems per plant; with compound branches in proximal nodes; about 6 to 8 branches per stem, branches to about 10 cm long and 2 mm across at base;

Stem color: Lower portion between RHS 145A and RHS 146D, with the upper portion in heavy sun exposure having light to moderate blush of nearest RHS N186C;

Nodes: Average about 4 cm apart with the greatest distance in the middle of the stem; about 10 nodes per stem before flowers;

Node color: Same as surrounding stem;

Inflorescence: Cymosely clustered with many flowers typically branched at verticillasters in the 8 to 10 upper nodes; about 10 to 40 flowers per node and about 100 to 250 flowers per inflorescence stem or peduncle;

Peduncle: Flowering portion curving upwardly; flowers on one verticillaster flowering over a prolonged period; flower portion in distal 20 cm and 4 cm wide;

Peduncle color: Nearest RHS 146C proximally and distally nearest RHS 146B with a strong blush of RHS 183C;

Pedicel: Sessile to 1 mm long and 0.3 mm diameter; puberulent; cylindrical; upwardly;

Pedicel color: When present nearest RHS 138A with a moderate blush of nearest RHS 183D;

Flower bud: Arcuate clavate; about 11 mm long, 5 mm tall, 3.5 mm wide in bulb portion, and 1.5 mm diameter at base; abaxial surface glandular to pubescent;

Flower bud color: Petal portion nearest RHS 86D; calyx portion nearest RHS 146B with a heavy blush of nearest RHS N79B dorsal side and veins;

Flowers: Zygomorphic; perfect; bilabiate; sympetalous with basal 11 mm fused; lips opening to form about a 60 to 80-degree angle to each other; 15 mm long and 12 mm tall and 8 mm wide; in dense verticillasters;

*Upper lip.*—With two lobes; puberulent on abaxial surface, glabrous adaxial; lobes about 2 mm long and 2 mm wide above fusion; lobes with rounded apex; total size of lip about 15 mm long and about 5.5 mm wide at fusion.

*Lower lip.*—Consisting of three lobes; adaxial glabrous, abaxial puberulent proximally and glabrous distally; center and largest lobe slightly concave to flattened with rounded apex and crenate margin having seven indentations of about 1 mm deep in center and the three lateral incisions to about 0.5 mm deep overall about 8 mm wide near apex and 4 mm long; two side lobes with rounded apices and entire margin; center lobe to about 15 mm long in total, 8 mm long from fusion, and up to 9 mm across when flattened; side lobes 2 mm long from fusion and 4 mm across; micro-puberulent abaxial and glabrous near margin, glabrous adaxial except a pubescent tuft of white hairs nearest NN155D about 1.0 mm long in the center.

*Young petal color.*—Upper lip adaxial free portion between RHS N87B and RHS N87C and abaxial portion between RHS 86C and N87D; lower lip adaxial proximally nearest RHS 86C, distally nearest RHS N88B maculate with spots about 0.2 mm to 1 mm diameter and sometimes fused of between RHS 83B and 86A, abaxial nearest RHS N87A.

*Mature petal color*.—Upper lip adaxial nearest RHS N88C and abaxial between RHS N87D and N88C; lower lip adaxial side lobes nearest RHS N88C maculate with spots between RHS N87A and RHS N87B, abaxial side lobes between RHS N88C and RHS N87D; center lobe adaxial nearest RHS N87B with spots nearest RHS N87A, abaxial center lobe between RHS N88C and RHS N87D;.

*Corolla tube color*.—Adaxial and abaxial proximal 5 mm nearest RHS NN155D, distal 5 mm adaxial nearest RHS N88D with spots on lower lip portion of nearest RHS N88C, distal 5 mm abaxial between RHS 85D and RHS N88D.

Calyx: Synsepalous; 5-merous fused into a tube in basal 6 to 8 mm; to 10 mm long, 3 mm tall, and 2 mm across at apex;

Sepals: Five; synsepalous; acute apex; basal 6 to 8 mm fused, free in distal 2 mm; margin ciliolate; with about 3 conspicuous longitudinal veins; glabrous adaxial, pubescent abaxial; persistent after flower drop;

Sepal color: Adaxial basal 2 mm nearest RHS 193A and distal 3 mm nearest RHS 146B with middle portion nearest RHS 144D with veins nearest RHS 146B; abaxial; abaxial basal 2 mm nearest RHS 193A, distal 3 mm nearest RHS 146D and middle nearest RHS 145C with a light blush of nearest RHS 86B and veins nearest RHS 146B;

Gynoecium: Single compound ovary with two carpels, single gynobasic style, and bifurcate stigma;

*Style*.—About 15 mm long and 0.3 mm diameter; color proximally nearest RHS NN155D with distal 2 mm nearest RHS N87B.

*Stigma*.—Bifurcate in distal 1 mm and about 0.1 mm diameter; with sharply acute apex; color nearest RHS N92C.

*Ovary*.—Four-lobed, each lobe ovoid, about 1 mm long and 0.5 mm across; color between RHS 145A and RHS N144D.

Androecium: Four;

*Filaments*.—Cylindrical; straight; in two sets of two; longer set to 14 mm long and 0.3 mm diameter, adnate to petals in basal 11 mm, free in distal 3 mm; shorter set to 12 mm long and 0.3 mm diameter, adnate in basal 7 mm, free in distal 5 mm; color proximally nearest RHS NN155D and distally nearest RHS N87D.

*Anthers*.—Oblong ellipsoidal; 1 mm long and 0.5 mm across; color between RHS N92B and RHS N92A.

*Pollen*.—Abundant; color nearest RHS NN155B.

Flowering period: In Western Michigan beginning in late spring and repeating until fall frost without deadheading; individual flowers remain open for about three days;

Flower fragrance: None detected;

Flower attitude: Outwardly;

Fruit and seed: Prolific; nutlets; flattened ellipsoid; about 1.5 mm long, 1 mm across, and 0.5 mm thick; nearest RHS 200A;

Pest and disease susceptibility: Typically, not prone to browsing by deer or rodents but no resistance beyond that which is typical for *Nepeta*.

I claim:

1. A new and distinct hardy perennial *Nepeta* plant named 'Chartreuse on the Loose' essentially as herein described and illustrated.

* * * * *